(12) United States Patent
Usala

(10) Patent No.: US 7,700,660 B2
(45) Date of Patent: Apr. 20, 2010

(54) METHOD OF TREATING CHRONIC ULCERS

(75) Inventor: Anton-Lewis Usala, Winterville, NC (US)

(73) Assignee: Encelle, Inc., Greenville, NC (US)

( * ) Notice: Subject to any disclaimer, the term of this patent is extended or adjusted under 35 U.S.C. 154(b) by 1592 days.

(21) Appl. No.: 09/870,414

(22) Filed: May 30, 2001

(65) Prior Publication Data

US 2002/0077277 A1 Jun. 20, 2002

Related U.S. Application Data

(60) Provisional application No. 60/208,116, filed on May 31, 2000.

(51) Int. Cl.
*A61K 8/65* (2006.01)
(52) U.S. Cl. .................. 514/774; 530/354; 424/422; 424/426
(58) Field of Classification Search .............. 424/400, 424/424, 425, 426; 514/2, 801; 530/354, 530/356
See application file for complete search history.

(56) References Cited

U.S. PATENT DOCUMENTS

| | | | |
|---|---|---|---|
| 4,198,479 A | 4/1980 | Tytell et al. | |
| 4,520,821 A | 6/1985 | Schmidt et al. | |
| 4,657,866 A | 4/1987 | Kumar | |
| 4,696,286 A | 9/1987 | Cochrum | |
| 4,797,213 A | 1/1989 | Parisius et al. | |
| 4,902,295 A | 2/1990 | Walthall et al. | |
| 4,950,483 A | 8/1990 | Ksander et al. | |
| 4,957,902 A | 9/1990 | Grinnell | |
| 5,021,349 A | 6/1991 | Drouet et al. | |
| 5,059,588 A * | 10/1991 | Pickart ............... | 514/12 |
| 5,079,160 A | 1/1992 | Lacy et al. | |
| 5,128,360 A | 7/1992 | Cerami et al. | |
| 5,246,971 A | 9/1993 | Williamson et al. | |
| 5,263,983 A | 11/1993 | Yoshizato et al. | |
| 5,322,790 A | 6/1994 | Scharp et al. | |
| 5,358,969 A | 10/1994 | Williamson et al. | |
| 5,457,093 A | 10/1995 | Cini et al. | |
| 5,487,899 A * | 1/1996 | Davis ................. | 424/443 |
| 5,591,709 A | 1/1997 | Lindenbaum | |
| 5,605,938 A | 2/1997 | Roufa et al. | |
| 5,645,591 A | 7/1997 | Kuberasampath et al. | |
| 5,716,404 A | 2/1998 | Vacanti et al. | |
| 5,824,331 A * | 10/1998 | Usala ................. | 424/424 |
| 5,830,492 A | 11/1998 | Usala | |
| 5,834,005 A | 11/1998 | Usala | |
| 5,840,059 A | 11/1998 | March et al. | |
| 5,852,009 A | 12/1998 | Cerami et al. | |
| 5,855,617 A | 1/1999 | Orton | |
| 6,046,160 A | 4/2000 | Obi-Tabot | |
| 6,132,759 A | 10/2000 | Schacht et al. | |
| 6,197,330 B1 | 3/2001 | Rees et al. | |
| 6,231,881 B1 * | 5/2001 | Usala et al. ........... | 424/425 |
| 6,238,888 B1 | 5/2001 | Gentz et al. | |
| 6,261,587 B1 * | 7/2001 | Usala ................. | 424/426 |
| 6,299,898 B2 | 10/2001 | Rees et al. | |
| 6,372,494 B1 | 4/2002 | Naughton et al. | |
| 6,713,079 B2 * | 3/2004 | Usala ................. | 424/426 |

FOREIGN PATENT DOCUMENTS

| | | |
|---|---|---|
| DE | 44 31 598 A1 | 3/1996 |
| EP | 0 213 908 A2 | 3/1987 |
| EP | 0 526 756 A | 2/1993 |
| EP | 0 564 786 A | 10/1993 |
| EP | 0 363 125 A2 | 10/1998 |
| WO | WO 91/09119 A1 | 6/1991 |
| WO | WO 92/19195 | 11/1992 |
| WO | WO 93/16685 | 9/1993 |
| WO | WO 93/16717 A1 | 9/1993 |
| WO | WO 93/24112 A1 | 12/1993 |
| WO | WO 94/03154 A1 | 2/1994 |
| WO | WO 94 08702 | 4/1994 |
| WO | WO 94/15589 A1 | 7/1994 |
| WO | WO 95/14037 | 5/1995 |
| WO | WO 95/19430 A1 | 7/1995 |
| WO | WO 97/20569 A | 6/1997 |
| WO | WO 97 39107 | 10/1997 |
| WO | WO 98/55161 | * 12/1998 |
| WO | WO 98/55161 A1 | 12/1998 |
| WO | WO 00/02596 A1 | 1/2000 |

(Continued)

OTHER PUBLICATIONS

Miller, Fred. 'Essential of Pressure Ulcer Treatment' J. dermatol. Surg. Oncol. vol. 19, 759-763. 1993.*

(Continued)

*Primary Examiner*—Anish Gupta
(74) *Attorney, Agent, or Firm*—Alston & Bird LLP

(57) ABSTRACT

The invention provides a method of treating a chronic ulcer, such as a diabetic ulcer, comprising administering a therapeutic amount of a hydrogel matrix to the ulcer, the matrix composition comprising gelatin and a long chain carbohydrate. The matrix may further include polar amino acids, nitric oxide inhibitors and super oxide inhibitors. Injection is a preferred method of administration. The matrix may be injected into one or more locations within the ulcer, underneath the ulcer and/or around the periphery of the ulcer.

54 Claims, 5 Drawing Sheets

FOREIGN PATENT DOCUMENTS

| WO | WO00/02999 | * | 1/2000 |
|----|------------|---|--------|
| WO | WO 00/02999 A2 | | 1/2000 |

OTHER PUBLICATIONS

Jude et al. The role of nitrix oxide synthase isoforms and arginase in the patoogenesis of fiabetic foot ulcers: possible modulatory effects by transforming growth factor beta 1. Diabetologia, vol. 42, 748-757, 1999.*

Mansbridge et al. Three Dimensional Fibroblast Culture Implant for the Treatment of Diabetic Foot Ulcers: Metabolic Activity and Therapeutic Range. Tissue Engineering, vol. 4, No. 4, pp. 403-414. 1998.*

Hubbell et al., "Tissue Engineering," *Chemical & Engineering News*, (Mar. 13, 1995), pp. 42-54.

Isner et al., "Therapeutic Angiogenesis," *Frontiers in Bioscience*, vol. 3 (May 5, 1998) pp. 49-69.

Pennisi et al., "Mice Null for Sox18 Are Viable and Display a Mild Coat Defect", *Molecular and Cellular Biology*, Dec. 2000, pp. 9331-9336, vol. 20, No. 24.

Ramsey et al., "Incidence, Outcomes, and Cost of Foot Ulcers in Patients with Diabetes", *Diabetes Care*, Mar. 1999, pp. 382-387, vol. 22, No. 3.

Ravin et al., "Long- and Short-Term Effects of Biological Hydrogels on Capsule Microvascular Density around Implants in Rats", *Neovascularization in Capsules*, Apr. 12, 2001, pp. 313-318.

U.S. Appl. No. 09/766,330, filed Jan. 19, 2001, Usala.

* cited by examiner

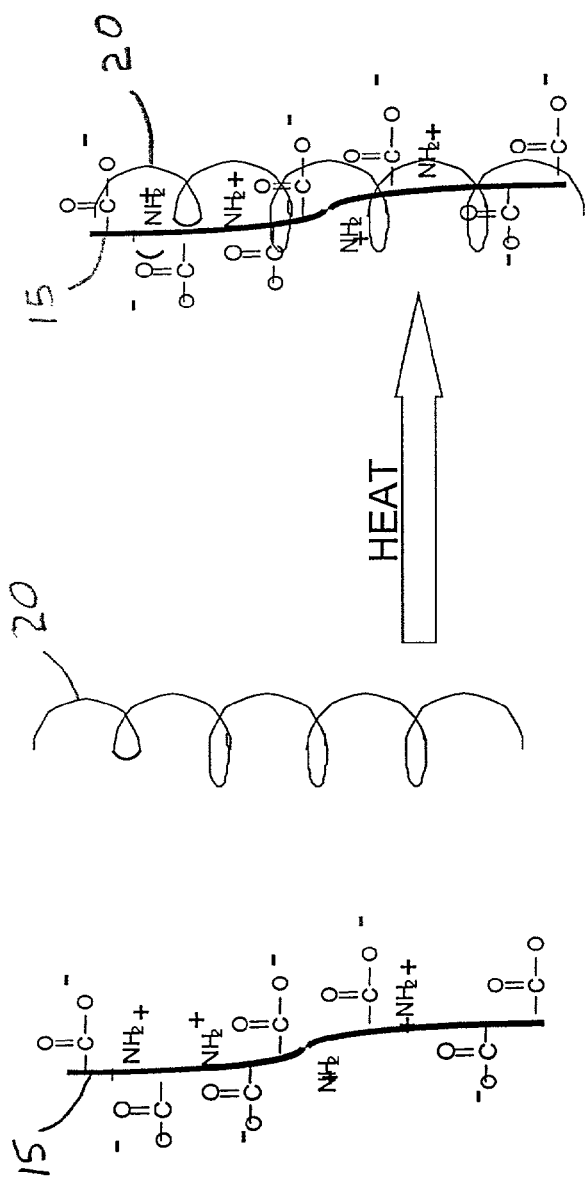
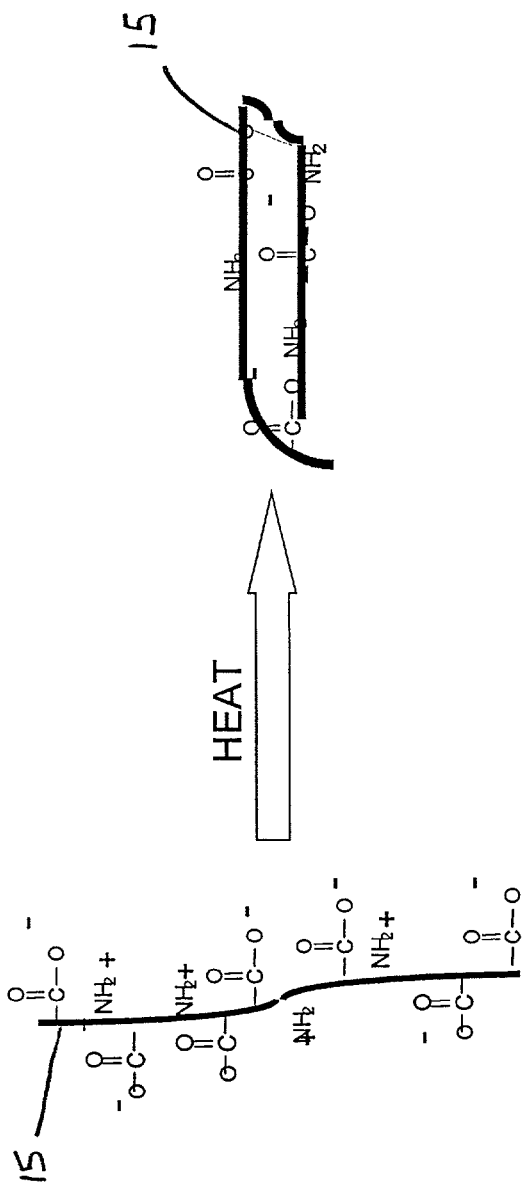
FIG. 2A
FIG. 2B

METHOD OF TREATING CHRONIC ULCERS

CROSS REFERENCE TO RELATED APPLICATIONS

This application claims the benefit of U.S. application Ser. No. 60/208,116, filed on May 31, 2000, which is incorporated by reference herein in its entirety.

FIELD OF INVENTION

The invention relates to methods of treating chronic ulcers, such as diabetic ulcers.

BACKGROUND OF THE INVENTION

There are over 15 million diagnosed cases of diabetes in the United States alone. According to the American Diabetes Association, about 60-70% of people with diabetes have mild to severe forms of diabetes-related nerve damage. Diabetic neuropathy is a condition that encompasses a wide range of dysfunction. Neuropathic ulcers or lesions of the foot resulting from diabetic neuropathy are a major cause of lower leg amputations. In fact, progression of diabetic foot ulcers is the leading cause of non-traumatic lower limb amputations in the United States. The risk of a leg amputation is 15-40 times greater for a person with diabetes.

Loss of protective sensation and repetitive trauma (e.g. walking) are major causes of such ulcers. Loss of tone in the small muscles of the feet cause changes in the architecture of the foot that ultimately result in increased pressure over the ball of the foot. This increased pressure causes calluses and eventually ulceration.

These lesions are associated with microcirculatory compromise, resulting in the breakdown of dermal integrity. The etiology is thought to be progressive endothelial vessel injury induced by chronic hyperglycemia. While neuropathy, trauma, and infection secondarily promote foot lesion extension, the underlying pathology for these conditions and the ulcer itself is chronic hyperglycemia resulting in compromised vascular flow to the skin. Once developed, these ulcers become chronic conditions lasting indefinitely. It is not unusual for ulcers of this type to persist for many years. Unlike common trauma-induced superficial wounds, chronic diabetic ulcers penetrate deep into the patient's tissue, often exhibiting penetration completely through the dermis, leaving the ulcer open and exposing underlying structures such as tendon, muscle or bone.

Current therapy for diabetic foot ulcers is inadequate, as evidenced by the high incidence of healing failure (See Ramsey et al., Diabetes Care 22:382-387, 1999). Conventional therapies include debridement of necrotic tissue, repeated sterile dressings, use of orthotic devices to reduce pressure, bed rest, and aggressive use of antibiotics to fight infection. Conventional therapy does not address the underlying pathology of microangiopathy in the lower extremity, but seeks to provide enough covering to prevent ulcer extension and possible amputation. Cell-based coverings are sometimes used to treat ulcers, such coverings including autologous skin flaps, skin grafts, or cultured skin layers such as APLIGRAF™. However, providing a covering that may or may not assist in closure does nothing to treat the underlying pathology, which is compromised circulation in combination with compromised sensation. As such, the rate of recurrence of healed ulcers is as high as 80%. There remains a need in the art for therapeutic methods for treating chronic ulcers, such as diabetes-related ulcers.

SUMMARY OF THE INVENTION

It has been discovered that the matrix described herein is capable of successfully treating and healing chronic ulcers, such as ulcers resulting from diabetes-related vasculoneuropathy. Although ulcers of this type are often resistant to conventional wound treatments, the method of the present invention can heal chronic lesions or ulcers in a matter of days or weeks. The present invention involves the administration of a therapeutic amount of a hydrogel matrix to the ulcer in a manner that exposes polar groups of the basement membrane of the patient's tissue to the components of the matrix (e.g. by injection).

The matrix of the invention preferably comprises a gelatin component, such as denatured collagen, at a concentration of about 0.01 to about 40 mM. The matrix also includes a long chain carbohydrate, such as dextran. The preferably concentration of dextran is about 0.01 to about 10 mM. Preferred embodiments of the matrix further include an effective amount of polar amino acids, one or more nitric oxide inhibitors, such as L-cysteine or L-arginine analogues, and a superoxide inhibitor, such as EDTA or salts thereof.

In a preferred embodiment, the administering step comprises injecting the matrix into one or more superficial locations within the ulcer, superficial locations around the periphery of the ulcer, and locations underneath the ulcer. Typically, the total therapeutic amount comprises about 1 to about 60 ml.

BRIEF DESCRIPTION OF THE DRAWINGS

Figure 1:
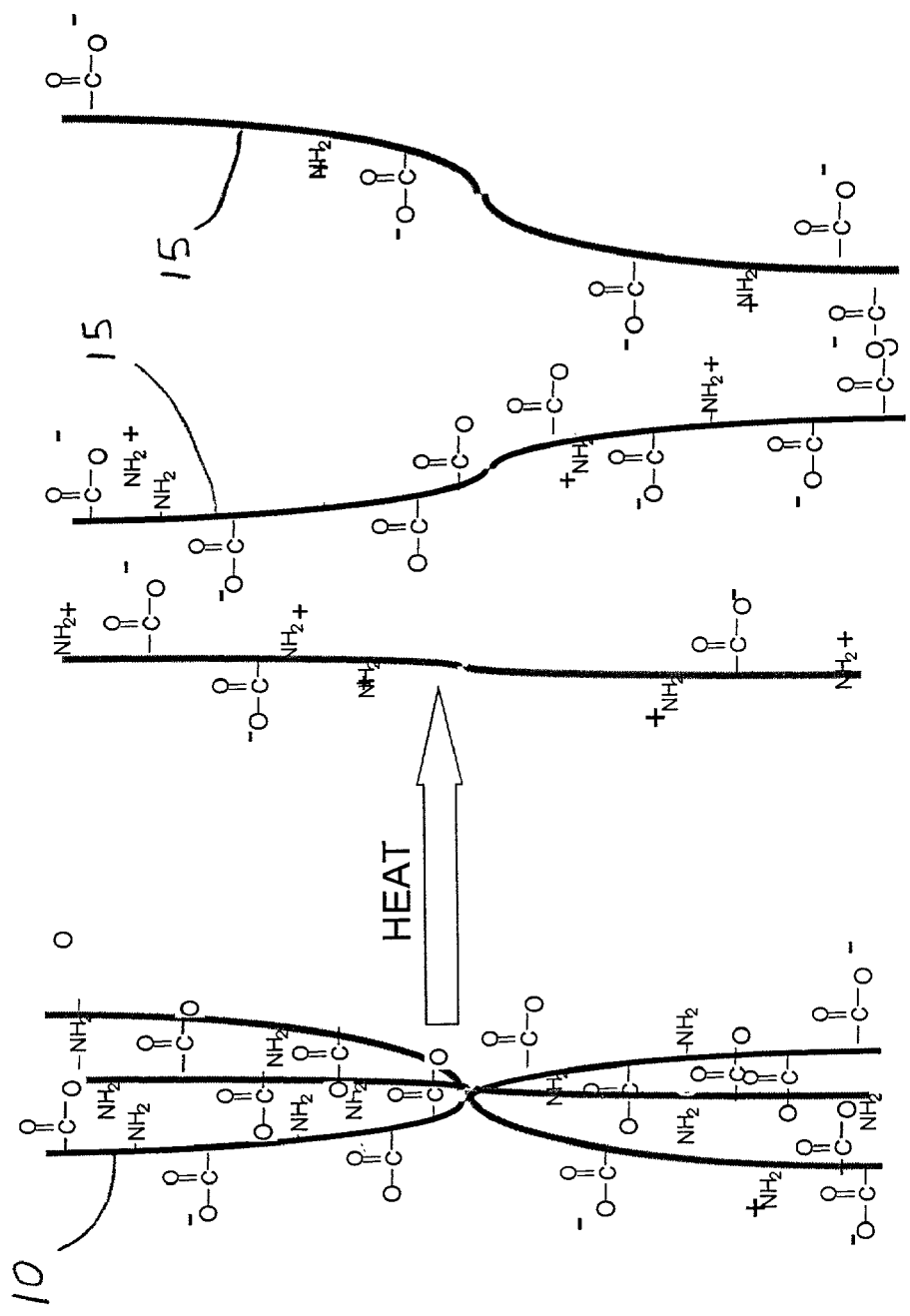
Figure 3:
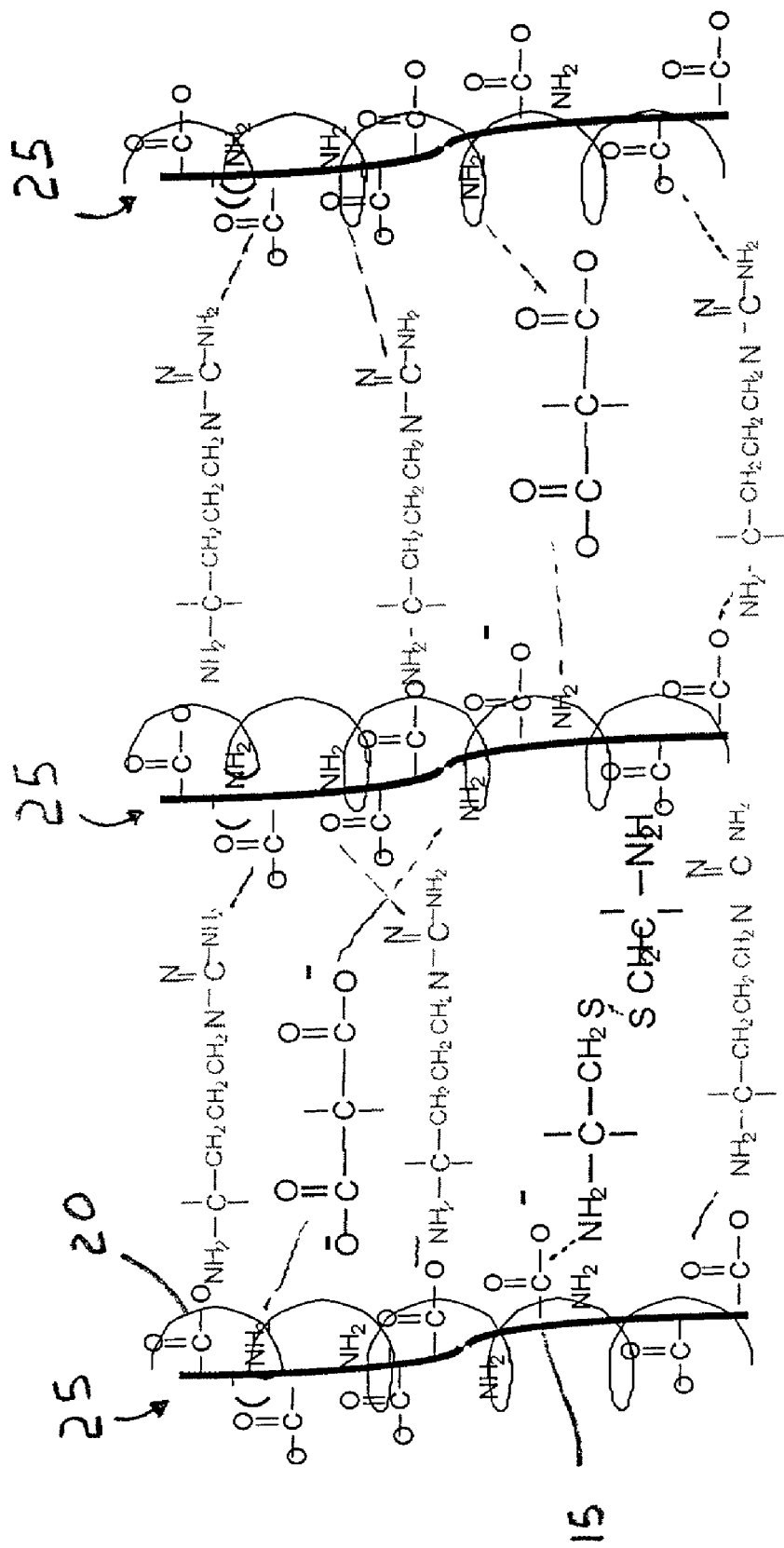
Figure 4:
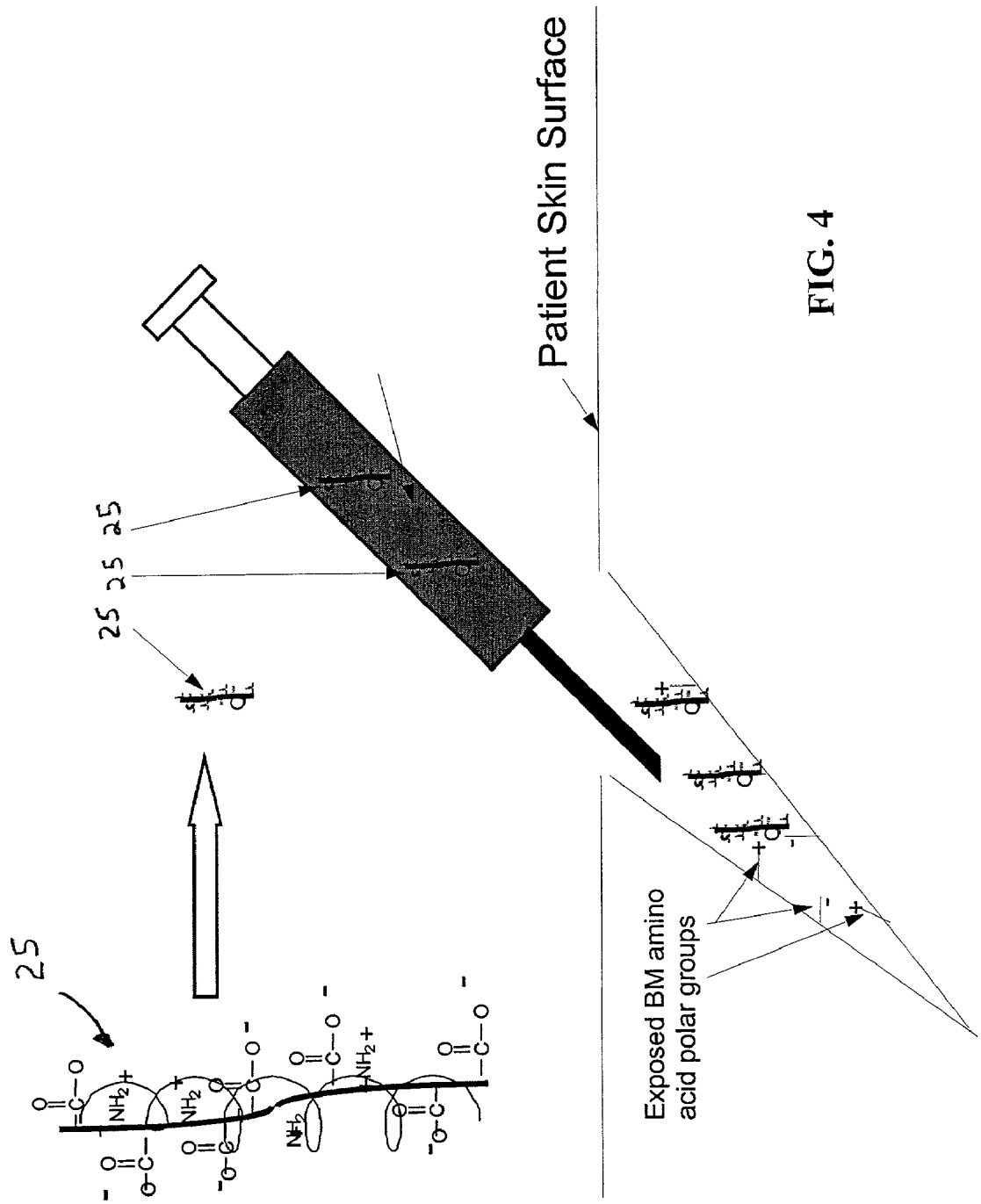
Figure 5:
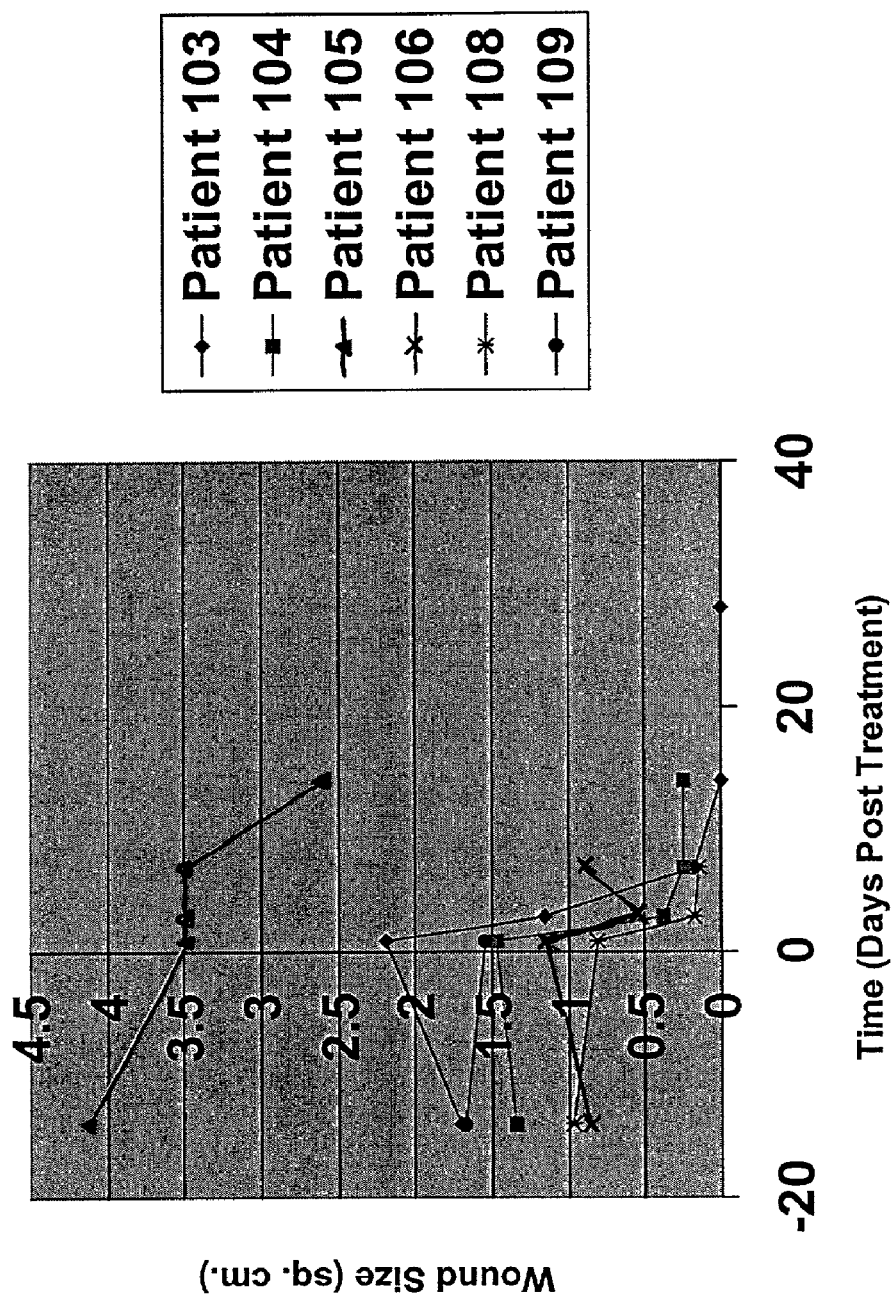

Having thus described the invention in general terms, reference will now be made to the accompanying drawings, wherein:

FIG. 1 illustrates formation of open alpha chains derived from collagen monomers;

FIGS. 2A and 2B illustrate the effect of the association of the alpha chains with dextran;

FIG. 3 illustrates the effect of other matrix additives;

FIG. 4 illustrates binding of the matrix to the basement membrane (BM) of a patient; and FIG. 5 graphically illustrates the effect of the matrix of the invention on the size of diabetic foot ulcers.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Early in fetal development, a more open form of collagen (compared to tightly bound mature collagen) is associated with large carbohydrate molecules, and serves as the predominant tissue scaffolding. It is believed that attachment of differentiated or incompletely differentiated cells of mescenchymal origin to this polar, proteoglycan-like, collagen scaffolding results in a specific host tissue response. This response is to guide the differentiation of mesenchymal tissue into endothelial cells, subsequently organizing into blood vessels, and finally differentiating into primitive blood cells prior to the differentiation of bone marrow.

Although not bound by any particular theory, the present invention is intended to provide a matrix scaffolding designed to maximize the polar amino acid hydrogen bonding sites found in alpha chains derived from collagen. These alpha chains or gelatin are preferably derived from pig gelatin, and stabilized by 500,000 molecular weight dextran, or other long-chain carbohydrates, added while the alpha chains are heated. The positively charged polar groups of the collagen-derived alpha chains are then able to associate with the negatively charged —OH groups of the repeating glucose units found in the dextran. The gelatin and the dextran form a proteoglycan-type structure. FIGS. 1-4 illustrate the interaction between the various components of the preferred embodiment of the matrix of the invention and interaction between the matrix and the tissue of a patient.

FIG. 1 illustrates the creation of polar alpha chains 15 from tropocollagen 10 derived from mature collagen. Heating tropocollagen 10 disrupts the hydrogen bonds that tightly contain the triple stranded monomers in mature collagen. By breaking these hydrogen bonds, the polar amine and carboxylic acid groups are now available for binding to polar groups from other sources or themselves.

FIGS. 2A-2B illustrate stabilization of the matrix monomeric scaffolding by the introduction of a long-chain carbohydrate 20, such as dextran. As shown in FIG. 2B, without the long-chain carbohydrate 20, the alpha chain 15 will form hydrogen bonds between the amino and carboxylic acid groups within the linear portion of the monomer and fold upon itself, thus limiting available sites for cellular attachment. As depicted in FIG. 2A, the long-chain carbohydrate 20 serves to hold the alpha chain 15 open by interfering with this folding process.

FIG. 3 illustrates the effect of polar amino acids and/or L-cysteine added to stabilize the monomer/carbohydrate units 25 by linking the exposed monomer polar sites to, for example, arginine's amine groups or glutamic acid's carboxylic acid groups. Furthermore, disulfide linkages can be formed between L-cysteine molecules (thereby forming cystine), which in turn forms hydrogen bonds to the monomeric alpha chains 15. The hydrogen bonds formed between these additional amino acids and monomer/dextran units 25 are broken when the matrix is liquefied upon heating, and the polar groups are freed to attach the monomer/dextran units to exposed patient tissue surfaces upon injection. In preferred embodiments, EDTA or a salt thereof is also present to chelate divalent cations and thereby prevent divalent cations from being preferentially attracted to the exposed polar groups of the monomer/carbohydrate units 25 to the exclusion of the polar amino acids.

FIG. 4 shows attachment of the matrix to patient tissue by hydrogen bonding to exposed tissue amino acids. Exposure of these amino acids is easily achieved by tearing of the tissue with a hypodermic needle at the time of injection. The exposed polar groups of the basement membrane (BM) of the patient's tissue readily bind to the solid, scaffolding portion of the matrix enhanced by the polar amino acids. The aqueous portion is believed to be absorbed over a period of minutes to hours at normal body temperature.

Normally, the tearing of tissue secondary to injection trauma stimulates production and release of nitric oxide, initiating recruitment of immune and inflammatory cells that phagocytise or release chemicals to destroy foreign substances. By providing local and temporal inhibition of nitric oxide and superoxide release and production, nitric oxide inhibitors, such as aminoguanidine and cysteine, and superoxide inhibitors, such as EDTA, allow the collagen derived alpha chain/dextran units 25 to bind and become integrated on the exposed tissue surface. The alpha chain/dextran units 25 then serve as the scaffolding on which formerly differentiated host cells de-differentiate into "mesenchymoid" morphology. This de-differentiation process is followed by integration of these incompletely differentiated cells into host tissue. These mesenchymoid cells are then able to promote areas of their genome that leads to differentiation into fibroblasts, endothelial cells, and primitive blood forms, which results in tissue healing and regeneration.

By providing a proteoglycan-like scaffolding similar to that found in the early stages of fetal development, and using structural stabilizers that serve a secondary purpose in enhancing host response to the scaffolding upon injection, the matrix serves as a biocompatible device capable of increasing vascularization and promoting wound healing and local tissue regeneration, even in the case of diabetic foot ulcers unresponsive to conventional ulcer treatments. Because the matrix promotes tissue regeneration, as occurs during embryogenesis and fetogenesis where similar types of scaffolding are present, it has now been discovered that the matrix of the invention can be used to successfully treat chronic ulcers that fail to respond to conventional would therapy, such as ulcers caused by diabetes, ulcers caused by chronic pressure (decubitus ulcers), venous stasis ulcers, or trauma-induced ulcers accompanied by surrounding vascular damage.

Components of the Matrix

The matrix comprises a gelatin component. Although denatured collagen is the preferred gelatin component, other gelatinous components characterized by a backbone comprised of long chain sequences of amino acids having polar groups whose intramolecular hydrogen bonds can be broken in order to expose the polar groups to interaction with other molecules can be used. For example, boiled agarose, alginate, keratin, aminoglycans, proteoglycans and the like could be used as the gelatin component. In one embodiment, the gelatin is porcine gelatin from partially hydrolyzed collagen derived from skin tissue.

The gelatin is present at a concentration of about 0.01 to about 40 mM, preferably about 0.05 to about 30 mM, most preferably about 1 to about 5 mM. Advantageously, the gelatin concentration is approximately 1.6 mM. The above concentrations provide a solid phase at storage temperature (below about 33° C.) and a liquid phase at treatment temperature (about 35 to about 40° C.). Intact collagen may be added in small amounts to provide an additional binding network. The final concentration of intact collagen is from about 0 to about 5 mM, preferably 0 to about 2 mM, most preferably about 0.05 to about 0.5 mM.

A long chain carbohydrate having a molecular weight of about 20,000 to about 1,000,000 Daltons is added to the gelatin component. Although dextran is a preferred carbohydrate, other high molecular weight carbohydrates may be used, such as amylopectin. The dextran loosely polymerizes around the gelatin component, thereby facilitating cell attachment by preventing folding of the gelatin scaffolding. The long chain carbohydrate is present at a concentration of about 0.01 to about 10 mM, preferably about 0.01 to about 1 mM, most preferably about 0.01 to about 0.1 mM. In one embodiment, dextran is present at a concentration of about 0.086 mM.

The gelatin/long chain carbohydrate component of the matrix of the present invention is mixed with a liquid composition. The liquid composition is preferably based upon a standard culture medium, such as Medium 199, supplemented with additives as described below.

The matrix preferably includes an effective amount of polar amino acids, such as arginine, lysine, histidine, glutamic acid, and aspartic acid, which further enhance the bioadhesiveness of the matrix. An effective amount is the amount necessary to increase the rigidity of the matrix and allow direct injection of the matrix into the patient. In one embodiment, the concentration of polar amino acids is about 3 to about 150 mM, preferably about 10 to about 65 mM, and more preferably about 15 to about 40 mM.

Advantageously, the added polar amino acids comprise L-glutamic acid, L-lysine, L-arginine, or mixtures thereof. The final concentration of L-glutamic acid is about 2 to about 60 mM, preferably about 5 to about 40 mM, most preferably about 10 to about 20 mM. In one embodiment, the concentration of L-glutamic acid is about 15 mM. The final concentration of L-lysine is about 0.5 to about 30 mM, preferably about 1 to about 15 mM, most preferably about 1 to about 10 mM. In one embodiment, the concentration of L-lysine is about 5 mM. The final concentration of L-arginine is about 1 to about 40 mM, preferably about 1 to about 30, most preferably about 5 to about 15 mM. In one embodiment, the final concentration of L-arginine is about 10 mM.

Additionally, the matrix preferably contains one or more nitric oxide inhibitors. Nitric oxide inhibitor is defined as any composition or agent that inhibits the production of nitric oxide or scavenges or removes existing nitric oxide. Nitric oxide, a pleiotropic mediator of inflammation, is a soluble gas produced by endothelial cells, macrophages, and specific neurons in the brain, and is active in inducing an inflammatory response. Nitric oxide and its metabolites are known to cause cellular death from nuclear destruction and related injuries. Preferred nitric oxide inhibitors include L-cysteine, L-arginine analogues (such as aminoguanidine, N-monomethyl-L-arginine, N-nitro-L-arginine, D-arginine and the like), cystine, heparin, and mixtures thereof.

In one embodiment, the matrix contains L-cysteine. L-cysteine acts as a nitric oxide scavenger and provides disulfide linkages, which increase the matrix's rigidity and resistance to force. The final concentration of L-cysteine is about 5 to about 500 µM, preferably about 10 to about 100 µM, most preferably about 15 to about 25 µM. In one embodiment, the final concentration is about 20 µM.

Advantageously, aminoguanidine is also added to the matrix of the present invention. As indicated above, aminoguanidine is an L-arginine analogue and acts as a nitric oxide inhibitor. The final concentration of aminoguanidine is about 5 to about 500 µM, preferably about 10 to about 100 µM, most preferably about 15 to about 25 µM. In one embodiment, the final concentration is about 20 µM.

Additionally, the matrix of the present invention may include a superoxide inhibitor. A preferred superoxide inhibitor is ethylenediaminetetraacetic acid (EDTA) or a salt thereof. Superoxide is a highly toxic reactive oxygen species, whose formation is catalyzed by divalent transition metals, such as iron, manganese, cobalt, and sometimes calcium. Highly reactive oxygen species such as superoxide ($O_2^{31}$) can be further converted to the highly toxic hydroxyl radical ($OH^{31}$) in the presence of iron. By chelating these metal catalysts, EDTA serves as an antioxidant. EDTA is also a divalent cation chelator, which increases the rigidity of the matrix by removing inhibition of —$NH_2$ to —COOH hydrogen bonding. The concentration range for the superoxide inhibitor is about 0.01 to about 10 mM, preferably 1 to about 8 mM, most preferably about 2 to about 6 mM. In a preferred embodiment, the superoxide inhibitor is present at a concentration of about 4 mM.

Table 1 below lists particularly preferred key components of the matrix of the present invention along with suitable concentrations as well as preferred concentrations for each component.

TABLE 1

| Component | Concentration Range | Preferred Concentration |
| --- | --- | --- |
| L-glutamic acid | 2 to 60 mM | 15 mM |
| L-lysine | .5 to 30 mM | 5.0 mM |
| Arginine | 1 to 40 mM | 10 mM |
| Gelatin | 0.01 to 40 mM | 1.6 mM |
| L-cysteine | 5 to 500 µM | 20 µM |
| Aminoguanidine | 5 to 500 µM | 20 µM |
| Intact collagen | 0 to 5 mM | 0 mM |
| EDTA | 0.01 to 10 mM | 4 mM |
| Dextran | 0.01 to 10 mM | 0.086 mM |

Matrix Preparation

Place 835 ml of Medium 199 into a stirred beaker. While stirring, heat the solution to 50° C. Pipette 63.28 µl of cysteine, 1 ml of L-glutamine and 200 µl of aminoguanidine into the stirred beaker. Add the following gamma-irradiated dry raw materials: 120 grams of denatured collagen, 50 grams of dextran, and 0.1 grams of intact collagen. Use a glass stirring rod to aid mixing of the dry materials into solution. Pipette 8 ml of EDTA into the solution. Pipette 5 ml of L-glutamic acid, 5 ml of L-lysine acetate, and 5 ml of arginine HCl into the stirred beaker. Note that the solution will turn yellow. Use 10% NaOH to adjust the pH of the matrix solution to a final pH of 7.40±0.1. Osmolality is preferably adjusted with sodium chloride and/or sterile water as need to a final osmolality of about 200 to about 400 mOsm.

Treatment Method

Preferably, a therapeutic amount of the matrix of the invention is administered to a patient suffering from a ulcer, such as a chronic foot ulcer caused by diabetes-related vasculoneuropathy. The patient can be any animal, including mammals such as dogs, cats and humans. The term "therapeutic amount" refers to the amount required to promote ulcer healing via tissue regeneration as evidenced by, for example, reduction in the size of the ulcer. The therapeutic amount will be primarily determined by the size of the chronic lesion. Typically, the volume of matrix applied to the ulcer is about 1 to about 60 mL. In other terms, the therapeutic amount is approximately 0.1 to about 5 ml/2.5 cm of the "injection track," which is the total linear distance that will be traversed during matrix administration. Preferably, the therapeutic amount is sufficient to provide a uniform scaffolding for cellular attachment and differentiation in the subdermal/subcutaneous interface beneath the ulcer crater and under the ulcer periphery. In the case of a diabetic foot ulcer, wherein the compromised microvasculature extends to contiguous tissue underneath the ulcer, the physician must use clinical judgment to inject subdermal or subcutaneous tissues beneath the ulcer that he/she feels would benefit from regeneration of healthy tissue. The matrix is warmed to a temperature of about 35 to about 40° C. prior to administration in order to liquefy the matrix.

The method of application of the matrix should result in contact between the matrix and exposed polar groups of the basement membrane of the patient's tissue. A preferred method of administering the matrix is by injection, wherein the needle itself provides the necessary tearing of tissue that exposes cellular attachment sites capable of integration with the injected matrix.

In one embodiment, the matrix is injected intradermally or subdermally and circumferentially around the perimeter of the lesion (skin side) as well as intralesionally across the lesion width in parallel tracks separated by about 1 cm. Thus, a typical dose consists of multiple superficial injections at spaced locations around and/or within the lesion. The preferred target location of the superficial injections is the area of the dermal/subdermal tissue junction, which is typically about 0.5 to about 2.0 mm beneath the surface. The skin will be pierced superficially as if intending to give an intradermal injection, applying pressure on the plunger. The matrix will not flow at this juncture, so the needle should slowly be moved deeper at a wider angle until the matrix flows with gentle plunger pressure. At that point, the needle should be in the desired subdermal space. The plunger should be pulled back to ensure that the needle is not directly entering a vein or an artery. If the ulcer is a full thickness ulcer, that is, with no dermal tissue exposed in the wound center, then the intralesional matrix injections should be injected at the most superficial angle possible to allow the matrix to contact the surface tissue. In this approach, the needle will be visible as it is advanced just beneath the exposed ulcer surface and the surface will be visible expanded as the matrix volume is injected. As noted above, in addition to the superficial injections around and within the ulcer, it may be advisable to inject an additional volume of matrix underneath the ulcer.

If the initial injection does not fully heal the lesion, further injections can be made as needed. Examples of matrix injection dosage amounts for the superficial injections (visible surface of the ulcer) are given in Table 2 below.

TABLE 2

| Ulcer Diameter | Ulcer Area | Matrix Amount | Approximate No. of Injections |
|---|---|---|---|
| 1.0 cm | 0.8 cm$^2$ | 1.3 mL | 3 |
| 2.0 cm | 3.1 cm$^2$ | 2.5 mL | 5 |
| 3.0 cm | 7.1 cm$^2$ | 6.0 mL | 7 |
| 4.0 cm | 12.6 cm$^2$ | 9.4 mL | 9 |
| 5.0 cm | 19.6 cm$^2$ | 13.3 mL | 12 |
| 6.0 cm | 28.3 cm$^2$ | 18.1 mL | 15 |

EXPERIMENTAL

Example 1

Two diabetic vascular lesions on a spontaneously diabetic, hyperlipidemic dog were treated with a single injection of the matrix (having the approximate concentrations and ingredients listed in Table 1) around the perimeter and centrally within the lesion. The total volume of injected matrix was about 5-10 ml in each lesion. One lesion was located on the right rear elbow and the other was on the right rear paw. Two days post-injection, hyperemia was evident in both lesions, but no swelling or inflammation.

The lesion on the elbow was completely closed within 6 days, with new skin and hair growth over the site of the lesion. A biopsy of the site was taken seven months after treatment. Histologic views of the site showed intact epidermis, dermis, hair follicles, and vascularization in the area of treatment. Notably, there appeared to be no scar tissue as is found with normal healing, and regeneration of the "reticular" (amorphous) morphology of the dermal extracellular scaffolding surfaces was apparent. Of interest was the presence of Rete ridges at the epidermis-dermis interface, suggestive of complete healing. These data demonstrate the long-term effect of a single injection of the matrix, and the integration of the matrix into host response mechanisms.

The lesion on the paw was significantly smaller after six days. Of note was that the area that was not healed after six days had not been injected as the needle was inserted distally into the center of the wound. These data further demonstrate that the matrix-induced rapid tissue regeneration is dependent on binding of the matrix to host tissues. The ulcer closed by 21 days.

Example 2

In another study, two of three rabbits with partial thickness skin ulcers on the back secondary to surgical ligation of peripheral blood vessels received matrix injections (having the approximate concentrations and ingredients listed in Table 1) circumferentially and centrally within the ulcer. After four days, the two treated lesions were greatly reduced in size and by day 21 were completely healed. Of particular note is the hair regeneration that occurred in the treated rabbits. The third rabbit with an ulcer that was not treated with the matrix demonstrated incomplete healing of the original lesion at 21 days, with appearance of a new ulcer, and no hair growth. Ulcer closure in rabbits receiving the matrix is consistent with increased vascularization, and treatment of the underlying vascular compromise. New ulcer formation in the rabbit receiving standard care resulted from lack of adequate vascularization, as occurs in diabetic foot ulcer disease.

Example 3

The matrix of the invention was administered by injection to six human patients having chronic lesions that had been present for six months to twelve years. A single dose of matrix (having the approximate concentrations and ingredients listed in Table 1) was applied to multiple sites around the periphery of the ulcer and, in one case, within the ulcer as well. The amount of matrix applied was determined by ulcer size as described above. An EMLA® cream was applied prior to treatment to numb the injection sites. After treatment, a conventional ulcer dressing was applied and standard ulcer care procedures were followed. If clinically indicated, tissue debridement was conducted prior to injection. Lesion size and appearance were gauged at periodic intervals after treatment. As shown in FIG. 5, the size of the lesion was markedly reduced post-treatment in every patient. The results for each patient are described below.

Patient 103: This was the first study patient injected with the matrix. The treated ulcer was present for four years, refractory to aggressive conventional care as well as DERMAGRAFT. This was the only ulcer in the study injected superficially underneath the ulcer surface. The clinician chose to inject some of the matrix underneath the lesion as well in hopes of regenerating healthy vasculature in the supporting tissue bed. The ulcer was closed by Day 14 with continued maturation of new tissue appearance through Day 84.

Patient 104: This patient's ulcer was present for approximately two years, refractory to aggressive conventional therapy. This ulcer was injected under the surface of the ulcer at its margins only. While the wound appeared to be filling in and healing well, the center remained open on Day 56. Again, this supports the belief that the matrix regenerates tissue through direct contact. The patient died on Day 72, the death apparently caused by complications resulting from a history of chronic hypertension and diabetes (these conditions had led to hospitalization previously).

Patient 105: This patient had the least chronic ulcer in the study, its existence having been documented for only six months prior to entry into the study. Again, the ulcer surface was not disrupted during administration of the matrix. Instead, the ulcer was injected under the ulcer surface at the margins. While the ulcer substantially healed (an over 65% reduction in surface area by Day 28), it remained open at Day 84.

Patient 106: This patient's ulcer was refractory to multiple therapies for over one year. The injections did not pierce the ulcer surface, but consisted of more superficial injections along the ulcer perimeter, resulting in a "white halo" appearance. The white appearance is thought to be related to the transient local vasoconstriction induced by nitric oxide inhibitors and scavengers. This patient has had uncontrolled hypertension, and injured his leg during an unrelated fall. While the margins of the ulcer came closer to together, reducing the exposed surface area by 40% by four weeks, it did seem to stall in further closure, again related to not having the ulcer surface injected.

Patient 108: This patient's ulcer was the most chronic in this study, having been open for 12 years. Again, while the ulcer center was not disrupted, the perimeter of the ulcer was more superficially injected, with the formation of the "white halo" within minutes of the injection. Because the ulcer was smaller, with the margins closer together, this enabled the superficially injected margins to come together utilizing normal wound healing mechanisms of closure in addition to the matrix-induced tissue regeneration. The ulcer was fully closed by Day 56 with new tissue evident.

Patient 109: This patient had the best-documented history of ulcer treatment. The ulcer was two years old at the time of treatment and refractory to four APLIGRAF applications, REGRANEX, and 30 days in a hyperbaric oxygen chamber. The patient lesion again exhibited the "white halo" after superficial injection of the ulcer perimeter. After the first week, the patient felt encouraged and did considerable walking without orthotic footwear, which may have resulted in the apparent opening and closing observed. On Day 56, it was uncertain if the ulcer was totally closed, but it had at least dramatically diminished in size. Again as this ulcer was smaller than some of the other ulcers, it is believed to have closed because of normal wound healing mechanisms pulling the margins together in addition to matrix-induced tissue regeneration.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of treating an ulcer, comprising administering a therapeutic amount of a hydrogel matrix in liquid form to the ulcer, the matrix composition comprising gelatin and a long chain carbohydrate, wherein said administering step comprises injecting the hydrogel matrix into one or more locations in the area of the dermal/subdermal tissue junction beneath the ulcer or at the periphery of the ulcer.

2. The method of claim 1, wherein the matrix comprises about 0.01 to about 40 mM gelatin.

3. The method of claim 1, wherein the gelatin comprises denatured collagen.

4. The method of claim 1, wherein the long chain carbohydrate comprises dextran.

5. The method of claim 4, wherein the matrix comprises about 0.01 to about 10 mM dextran.

6. The method of claim 1, wherein the long chain carbohydrate has a molecular weight of about 20,000 to about 1,000,000 Daltons.

7. The method of claim 1, wherein the matrix further comprises an effective amount of polar amino acids selected from the group consisting of arginine, lysine, histidine, glutamic acid, and aspartic acid.

8. The method of claim 7, wherein the effective amount of polar amino acids comprises about 3 to about 150 mM of polar amino acids.

9. The method of claim 7, wherein the effective amount of polar amino acids comprises about 10 to about 65 mM of polar amino acids.

10. The method of claim 7, wherein the polar amino acids are selected from the group consisting of arginine, glutamic acid, lysine and mixtures thereof.

11. The method according to claim 10, wherein the matrix comprises:
   about 2 to about 60 mM of L-glutamic acid;
   about 0.5 to about 30 mM of L-lysine; and
   about 1 to about 40 mM of arginine.

12. The method of claim 11, wherein the matrix comprises:
   about 5 to about 40 mM of L-glutamic acid;
   about 1 to about 15 mM of L-lysine; and
   about 1 to about 30 mM of arginine.

13. The method according to claim 10, wherein the effective amount of polar amino acids comprises about 2 to about 60 mM of L-glutamic acid.

14. The method according to claim 10, wherein the effective amount of polar amino acids comprises about 1 to about 40 mM of arginine.

15. The method of claim 10, wherein the effective amount of polar amino acids comprises about 0.5 to about 30 mM of L-lysine.

16. The method of claim 1, wherein the matrix further comprises at least one nitric oxide inhibitor.

17. The method of claim 16, wherein the nitric oxide inhibitor is selected from the group consisting of L-cysteine, L-arginine analogues, cystine, heparin, and mixtures thereof.

18. The method of claim 16, wherein the nitric oxide inhibitor is present in an amount of about 5 to about 1000 µM.

19. The method of claim 16, wherein the nitric oxide inhibitor is present in an amount of about 20 to about 200 µM.

20. The method of claim 1, wherein the matrix further comprises about 5 to about 500 µM of L-cysteine.

21. The method of claim 20, wherein the matrix comprises about 15 to about 25 µM of L-cysteine.

22. The method of claim 1, wherein the matrix further comprises about 5 to about 500 µM of an L-arginine analogue.

23. The method of claim 22, wherein the L-arginine analogue comprises aminoguanidine.

24. The method of claim 22, wherein the matrix comprises about 15 to about 25 µM of an L-arginine analogue.

25. The method of claim 1, wherein the matrix further comprises a superoxide inhibitor.

26. The method of claim 25, wherein the superoxide inhibitor comprises EDTA or a salt thereof.

27. The method of claim 25, wherein the superoxide inhibitor is present in an amount of about 1 to about 8 mM.

28. The method of claim 1, wherein the gelatin comprises denatured collagen and the long chain carbohydrate comprises dextran.

29. The method of claim 1, wherein the therapeutic amount comprises about 1.0 to about 60 ml.

30. The method of claim 1, wherein the ulcer is a diabetic foot ulcer.

31. A method of treating an ulcer, comprising administering a therapeutic amount of a hydrogel matrix to the ulcer, the matrix composition comprising denatured collagen, dextran, and an effective amount of polar amino acids selected from the group consisting of arginine, lysine, histidine, glutamic acid, aspartic acid, and mixtures thereof, wherein said administering step comprises injecting the hydrogel matrix into one or more locations in the area of the dermal/subdermal tissue junction beneath the ulcer or at the periphery of the ulcer.

32. The method of claim 31, wherein the effective amount of polar amino acids comprises about 3 to about 150 mM of polar amino acids.

33. The method of claim 32, wherein the effective amount of polar amino acids comprises about 10 to about 65 mM of polar amino acids.

34. The method of claim 31, wherein the polar amino acids are selected from the group consisting of arginine, glutamic acid, lysine and mixtures thereof.

35. The method according to claim 34, wherein the matrix comprises:
about 2 to about 60 mM of L-glutamic acid;
about 0.5 to about 30 mM of L-lysine; and
about 1 to about 40 mM of arginine.

36. The method of claim 31, wherein the matrix further comprises at least one nitric oxide inhibitor.

37. The method of claim 36, wherein the nitric oxide inhibitor is selected from the group consisting of L-cysteine, L-arginine analogues, cystine, heparin, and mixtures thereof.

38. The method of claim 36, wherein the nitric oxide inhibitor is present in an amount of about 5 to about 1000 µM.

39. The method of claim 36, wherein the nitric oxide inhibitor is present in an amount of about 20 to about 200 µM.

40. The method of claim 31, wherein the matrix further comprises about 5 to about 500 µM of L-cysteine.

41. The method of claim 31, wherein the matrix further comprises about 5 to about 500 µM of an L-arginine analogue.

42. The method of claim 31, wherein the matrix further comprises a superoxide inhibitor.

43. The method of claim 42, wherein the superoxide inhibitor comprises EDTA or a salt thereof.

44. The method of claim 31, wherein the ulcer is a diabetic foot ulcer.

45. The method of claim 31, wherein said therapeutic amount comprises about 1.0 ml to about 60 ml.

46. A method of treating an ulcer, comprising administering a therapeutic amount of a hydrogel matrix in liquid form to the ulcer, the matrix composition comprising denatured collagen, dextran, L-cysteine, and an effective amount of polar amino acids selected from the group consisting of arginine, lysine, histidine, glutamic acid, aspartic acid, and mixtures thereof, wherein said administering step comprises injecting the hydrogel matrix into one or more locations in the area of the dermal/subdermal tissue junction beneath the ulcer or at the periphery of the ulcer.

47. The method of claim 46, wherein said therapeutic amount comprises about 1.0 mL to about 60 mL.

48. The method of claim 46, wherein the ulcer is a diabetic foot ulcer.

49. A method of treating an ulcer, comprising administering a therapeutic amount of a hydrogel matrix in liquid form to the ulcer, the matrix composition comprising gelatin, a long chain carbohydrate having a molecular weight of about 20,000 to about 1,000,000 Daltons, and at least one polar amino acid, wherein said administering step comprises injecting the matrix into one or more locations in the area of the dermal/subdermal tissue junction beneath the ulcer or at the periphery of the ulcer.

50. The method of claim 49, wherein the ulcer is a foot ulcer resulting from diabetes-related vasculoneuropathy.

51. The method of claim 1, further comprising the step of debriding the ulcer prior to said administering step.

52. The method of claim 1, wherein the ulcer is selected from the group consisting of ulcers resulting from diabetes-related vasculoneuropathy, decubitus ulcers, venous stasis ulcers, and trauma-induced ulcers accompanied by surrounding vascular damage.

53. The method of claim 31, wherein the ulcer is selected from the group consisting of ulcers resulting from diabetes-related vasculoneuropathy, decubitus ulcers, venous stasis ulcers, and trauma-induced ulcers accompanied by surrounding vascular damage.

54. The method of claim 46, wherein the ulcer is selected from the group consisting of ulcers resulting from diabetes-related vasculoneuropathy, decubitus ulcers, venous stasis ulcers, and trauma-induced ulcers accompanied by surrounding vascular damage.

* * * * *

UNITED STATES PATENT AND TRADEMARK OFFICE
CERTIFICATE OF CORRECTION

| | | |
|---|---|---|
| PATENT NO. | : 7,700,660 B2 | |
| APPLICATION NO. | : 09/870414 | |
| DATED | : April 20, 2010 | |
| INVENTOR(S) | : Usala | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2016 days.

Signed and Sealed this
Eleventh Day of January, 2011

David J. Kappos
*Director of the United States Patent and Trademark Office*